(12) United States Patent
Kopke (10) Patent No.: US 12,121,501 B2
(45) Date of Patent: Oct. 22, 2024

(54) METHODS FOR TREATING HEARING LOSS INCIDENT TO COCHLEAR IMPLANT SURGERY

(71) Applicant: HOUGH EAR INSTITUTE, Oklahoma City, OK (US)

(72) Inventor: Richard D. Kopke, Oklahoma City, OK (US)

(73) Assignee: Hough Ear Institute, Oklahoma City, OK (US)

( * ) Notice: Subject to any disclaimer, the term of this patent is extended or adjusted under 35 U.S.C. 154(b) by 367 days.

(21) Appl. No.: 17/275,581

(22) PCT Filed: Sep. 11, 2019

(86) PCT No.: PCT/US2019/050692
§ 371 (c)(1),
(2) Date: Mar. 11, 2021

(87) PCT Pub. No.: WO2020/056056
PCT Pub. Date: Mar. 19, 2020

(65) Prior Publication Data
US 2023/0157980 A1 May 25, 2023

Related U.S. Application Data

(60) Provisional application No. 62/730,431, filed on Sep. 12, 2018.

(51) Int. Cl.
*A61K 31/198* (2006.01)
*A61K 31/15* (2006.01)
(Continued)

(52) U.S. Cl.
CPC ............ *A61K 31/198* (2013.01); *A61K 31/15* (2013.01); *A61P 27/16* (2018.01); *A61P 41/00* (2018.01)

(58) Field of Classification Search
CPC ............ A61K 31/7076; A61K 31/7105; A61K 38/085; A61K 38/10; A61K 38/1825;
(Continued)

(56) References Cited

U.S. PATENT DOCUMENTS 5,488,145 A 1/1996 Carney
2009/0280153 A1 11/2009 Hunter et al.
(Continued)

FOREIGN PATENT DOCUMENTS

JP 2011-528558 A 11/2011
JP 2013-502461 A 1/2013
(Continued)

OTHER PUBLICATIONS

International Preliminary Report on Patentability issued in International Patent Application No. PCT/US2019/050692, dated Mar. 25, 2021.
(Continued)

*Primary Examiner* — Savitha M Rao
(74) *Attorney, Agent, or Firm* — Foley & Lardner LLP (57) ABSTRACT

Disclosed here is a method of alleviating negative effects of cochlear implant surgery in a subject in need thereof comprising administering effective amounts of 2,4-disulfonyl α-phenyl tertiary butyl nitrone (2,4-DSPBN) or a pharmaceutically acceptable salt thereof and N-acetylcysteine (NAC) or a pharmaceutically acceptable salt thereof to a subject prior to, during, and/or after undergoing cochlear implant surgery.

21 Claims, 3 Drawing Sheets

(51) Int. Cl.
*A61P 27/16* (2006.01)
*A61P 41/00* (2006.01)

(58) Field of Classification Search
CPC ...... A61K 9/1647; A61K 47/20; A61K 49/10; A61K 9/5094; C12N 15/113; C12N 2310/14; C12N 15/1137; C12N 2310/3517; C12N 2320/31; C12N 2320/32; C12N 15/88; C07K 14/475
See application file for complete search history.

(56) References Cited

U.S. PATENT DOCUMENTS

| | | |
|---|---|---|
| 2012/0172435 A1 | 7/2012 | Kopke et al. |
| 2016/0067220 A1 | 3/2016 | Garcia da Rocha et al. |
| 2017/0224635 A1 | 8/2017 | Kopke et al. |
| 2018/0000950 A1 | 1/2018 | Savel et al. |
| 2018/0117115 A1 | 5/2018 | Kopke et al. |

FOREIGN PATENT DOCUMENTS

| | | |
|---|---|---|
| JP | 2013-515752 A | 5/2013 |
| JP | 6308656 B2 | 4/2018 |
| WO | WO-2010/009732 A1 | 1/2010 |
| WO | WO-2011/028503 A1 | 3/2011 |
| WO | WO-2011/079841 A1 | 7/2011 |

OTHER PUBLICATIONS

Communication issued in co-pending European Patent Application No. 19859922.7, dated May 19, 2022.
Weaver, Funding Pours in for Investigational Hearing Treatments, *The Hearing Journal*, vol. 67, pp. 14-20 (Sep. 2014).
Yawn, et al., "Cochlear Implantation: A Biomechanical Prosthesis for Hearing Loss," *F1000 Prime Reports*, vol. 7(45), pp. 1-6 (2015).
Eastwood, et al., "Permanent and Transient Effects of Locally Delivered n-acetyl Cystein in a Guinea Pig Model of Cochlear Implantation," *Hearing Research*, vol. 259, pp. 24-30 (2010).
Kopke, et al., "NAC for Noise: From the Bench Top to the Clinic," *Hearing Research*, vol. 226, Issues 1-2, pp. 114-125 (Apr. 2007).
Shahripour, et al., "N-acetylcysteine (NAC) in neurological disorders: mechanisms of action and therapeutic opportunities," *Brain and Behavior*, vol. 4(2), pp. 108-122 (2014).
Dodd, et al., "N-acetylcysteine for antioxidant therapy: pharmacology and clinical utility," Expert Opin Biol Ther., vol. 8(12), pp. 1955-1962 (2008).
Franco, et al., "Apoptosis and Glutathione: Beyond an Antioxidant," *Cell Death and Differentiation*, vol. 16, pp. 1303-1314 (2009).
Chen, et al., "Inhibitory Effect on Cerebral Inflammatory Response following Traumatic Brain Injury in Rats: A Potential Neuroprotective Mechanism of N-Acetylcysteine," *Mediators of Inflammation*, vol. 2008(716458), 8 pages (Mar. 2008).
Lindblad, et al., "The Efficacy of N-acetylcysteine to Protect the Human Cochlea from Subclinical Hearing Loss Caused by Impulse Noise: A Controlled Trial," *Noise Health*, vol. 13, No. 55, pp. 392-401 (2011).
Kopke et al., "Efficacy and safety of N-acetylcysteine in prevention of noise induced hearing loss: A randomized clinical trial," Hearing Research, vol. 323, pp. 40-50 (2015).
Li et al., "N-Acetylcysteine Downregulation of Lysyl Oxidase Activity Alleviating Bleomycin-Induced Pulmonary Fibrosis in Rats," *Respiration* 84(6): 509-517 (2012).
Shen et al., "N-acetylcysteine alleviates angiotensin II-mediated renal fibrosis in mouse obstructed kidneys," *Acta Pharmacol Sin.* 37(5): 637-644 (2016).
Klein et al., "Meningitis-associated hearing loss: Protection by adjunctive antioxidant therapy," Ann Neurol. 54(4): 451-458 (2003).
Wilk et al., "Impedance Changes and Fibrous Tissue Growth after Cochlear Implantation Are Correlated and Can Be Reduced Using a Dexamethasone Eluting Electrode," PLoS One 11(2): e0147552, 19 pages (2016).
Sugiura et al., "N-acetyl-l-cysteine inhibits TGF-β1-induced profibrotic responses in fibroblasts, pulmonary pharmacology and therapeutics," *Pulm Pharmacol Ther.* 22(6): 487-491 (2009).
Williams et al., "Investigating the free radical trapping ability of NXY-059, S-PBN and PBN," Free Radic. Res. 41:1047-1052 (2007).
Kotake et al., "Inhibition of NF-UB, iNOS mRNA, COX2 mRNA, and COX catalytic activity by phenyl-N-tert-butylnitrone (PBN)," *Biochim Biophys Acta.*, vol. 1448, pp. 77-84 (1998).
Duan et al., "Permeability of round window membrane and its role for drug delivery: our own findings and literature review," 4(1), pp. 34-43 (2009).
Floyd et al., "Anti-Cancer Activity of Nitrones and Observations on Mechanism of Action," *Anticancer Agents Med Chem.*, 11(4), pp. 373-379 (2011).
Foreign Action issued in Chinese Patent Application No. 201980057806.5, dated Jan. 4, 2024.
Eshraghi, et al., "A Novel Combination of Drug Therapy to Protect Residual Hearing Post Cochlear Implant Surgery," Acta Oto-Laryngologica, vol. 136, No. 4, pp. 420-424 (2016).
Ewert, et al., "HPN-07, a free radical spin trapping agent, protects against functional, cellular and electrophysiological changes in the cochlea induced by acute acoustic trauma," PLoS One, vol. 12, No. 8, 29 pages (2017).
Notice of Reasons for Rejection issued in co-pending Japanese Patent Application No. 2021-513852, dated Sep. 5, 2023.

METHODS FOR TREATING HEARING LOSS INCIDENT TO COCHLEAR IMPLANT SURGERY

CROSS-REFERENCE TO RELATED APPLICATIONS

This application is the U.S. National Stage of International Patent Application No. PCT/US2019/050692, filed Sep. 11, 2019, which claims priority from U.S. Provisional Patent Application No. 62/730,431, filed Sep. 12, 2018. The contents of these applications are hereby incorporated by reference in their entirety.

BACKGROUND

Hearing loss is a prevalent ailment, and about 17 percent of American adults report some degree of hearing loss. See Weaver et al., Hearing J. 67:14-20 (2014). Cochlear implants can provide hearing improvement for many patients suffering from hearing loss associated with exposure to ototoxins, noise trauma, or aging. See Yawn et al. F1000 Prime Report, 7:45 (2015). Cochlear implantation is a surgical procedure, wherein an electrode is inserted into the patient's cochlea, and the electrode is in close proximity with the auditory nerve system of the patient. The electrode can then transmit signals from an external microphone directly to the auditory system of the patient. Cochlear implantation, therefore, replaces the patient's normal hearing with a digital hearing system that allows the patient to regain hearing to some degree. Since cochlear implantation makes use of the patient's auditory nerve fibers, the patients eligible for this procedure must have normal and healthy auditory nerve cells for the cochlear implantation to function. Preservation of acoustic hearing to allow for the benefits of hybrid hearing technology requires preservation of inner and outer hair cells as well as afferent neurons within the cochlea despite cochlear implant insertion trauma.

Cochlear implantation is generally believed to destroy the natural mechanism of hearing and replace it with digital hearing. See Yawn et al. F1000 Prime Report, 7:45 (2015). Preserving the natural hearing leads to improved speech understanding, sound localization, and hearing in complex listening environments. To preserve the natural hearing mechanism, many different surgical procedures for the cochlear implant have been tried. These surgical procedures include methods to maximize atraumatic scala tympani insertion, methods relying on inserting the electrode into the cochlea through a naturally existing pathway, such as the round window, or methods relying on making a separate opening in the cochlea. However, no significant differences between surgical approaches on preserving the natural hearing in cochlear implant patients have been found.

In one study of hearing loss caused by cochlear implantation, local administration of N-acetylcystein (NAC) was found to have only modest and transient effects on improving hearing. Eastwood et al., Hearing Research 259: 24-30 (2010). This study noted only a barely significant hearing improvement with local NAC administration at the highest frequency only (32 kHz) at the 4-week post insertion time point, and no protective effect at lower frequencies whatsoever.

Accordingly, there remains a great medical need for alleviating the hearing deficiencies suffered by patients undergoing cochlear implant surgery.

SUMMARY

The present inventors successfully met the aforementioned medical need by providing methods and compositions for alleviating the negative effects of cochlear implant surgery in a subject in need thereof. Accordingly, at least one aspect of the invention relates to a method for alleviating the negative effects of cochlear implant surgery, comprising administering effective amounts of 2,4-disulfonyl α-phenyl tertiary butyl nitrone (2,4-DSPBN or HPN-07) or a pharmaceutically acceptable salt thereof and N-acetylcysteine (NAC) or a pharmaceutically acceptable salt thereof to a subject prior to, during, or after undergoing cochlear implant surgery.

In some embodiments, HPN-07 and NAC are administered locally to a subject suffering from the negative effects of cochlear implant surgery.

In some embodiments, HPN-07 and NAC are administered systemically to a subject suffering from the negative effects of cochlear implant surgery.

In some embodiments, HPN-07 and NAC are administered directly into the cochlea of a subject suffering from the negative effects of cochlear implant surgery.

In some embodiments, HPN-07 and NAC are administered orally to a subject suffering from the negative effects of cochlear implant surgery.

In some embodiments, HPN-07 and NAC are administered to a subject prior to the subject receiving the cochlear implantation of an electrode.

In another aspect of the invention, HPN-07 and NAC are administered to the subject prior to, during, and after the cochlear implant surgery. In some embodiments, HPN-07 and NAC are administered orally prior to, during, and after the surgery. In some embodiments, HPN-07 and NAC are administered intravenously or topically prior to the surgery, and HPN-07 and NAC are administered orally during and after the surgery. In some embodiments, HPN-07 and NAC are administered orally prior to the surgery, HPN-07 and NAC are administered intravenously at the time of or immediately prior to the surgery, and HPN-07 and NAC are administered orally after the surgery.

In some embodiments, a composition of HPN-07 and NAC and further comprising a lubricant are administered locally to a subject prior to the subject receiving the cochlear implantation of an electrode.

In some embodiments, a subject in need of cochlear implantation receives an electrode coated with a composition of HPN-07 and NAC.

In some embodiments, a subject in need of cochlear implantation receives a composition of HPN-07 and NAC further comprising a thermosensitive gel, such as a Pluronic hydrogel.

In some embodiments, a composition of HPN-07 and NAC is administered intra-tympanically prior to, during, or following cochlear implant surgery.

In some embodiments, the subject belongs to an adult population.

In some embodiments, the subject belongs to a pediatric population.

In some embodiments, the pediatric population is selected from neonates (birth to 1 month), infants (1 month to 2 years), developing children (2-12 years), and adolescents (12-16 years).

In one aspect, the present disclosure provides a method of treating a human subject diagnosed with sensorineural hearing loss prior to, while, and/or after undergoing cochlear implant surgery comprising administering to the subject effective amounts of 2,4-disulfonyl α-phenyl tertiary butyl nitrone (2,4-DSPBN) or a pharmaceutically acceptable salt thereof and N-acetylcysteine (NAC) or a pharmaceutically acceptable salt thereof prior to, during, and/or after undergoing cochlear implant surgery.

In some embodiments, the method of treating a human subject diagnosed with sensorineural hearing loss prior to, while, and/or after undergoing cochlear implant surgery further comprises performing auditory brainstem response (ABR) threshold recordings (measured by the sound pressure level in dB required to elicit an ABR response) at one or more test frequencies.

In some embodiments, the method of treating a human subject diagnosed with sensorineural hearing loss prior to, while, and/or after undergoing cochlear implant surgery further comprises comparing an ABR threshold recorded for the subject at the one or more test frequencies to an ABR threshold recorded for an untreated or control subject at the same one or more test frequencies.

In some embodiments, the ABR threshold recorded for the subject at the one or more test frequencies is lower compared to that of an untreated or control subject.

In some embodiments, the ABR threshold recordings are performed at one or more test frequencies ranging from 1 to 8 kHz.

In some embodiments, administration is carried out prior to, while, and after undergoing the cochlear implant surgery.

In some embodiments, the present disclosure provides a method of reducing a loss of a plurality of hair cells in a subject prior to, while, and/or after undergoing cochlear implant surgery comprising administering to the human subject effective amounts of 2,4-disulfonyl α-phenyl tertiary butyl nitrone (2,4-DSPBN) or a pharmaceutically acceptable salt thereof and N-acetylcysteine (NAC) or a pharmaceutically acceptable salt thereof prior to, while, and/or after undergoing cochlear implant surgery. In some embodiments, said hair cells comprise inner hair cells, outer hair cells, or both. In some embodiments, the loss of the plurality of outer hair cells at tonotopic frequency positions ranging from 1 to 8 kHz is reduced by at least about 70% compared that of untreated or control subjects.

In some embodiments, the loss of the plurality of inner hair cells at tonotopic frequency positions ranging from 1 to 8 kHz is reduced by at least about 38% compared to that of untreated or control subjects.

In some embodiments, the loss of the plurality of outer hair cells at tonotopic frequency positions ranging from 2 to 8 kHz is reduced by at least about 86% compared to that of untreated or control subjects.

In some embodiments, the loss of the plurality of inner hair cells at tonotopic frequency positions ranging from 2 to 8 kHz is reduced by at least about 64% compared to that of untreated or control subjects.

These and other features, together with the organization and manner of operation thereof, will become apparent from the following detailed description.

BRIEF DESCRIPTION OF DRAWINGS

FIG. 1 corresponds to Example 1 and demonstrates average threshold shifts at all frequencies tested (2, 4, 8, and 16 kHz) immediately and 4 weeks after cochlear implantation. The results shown in FIG. 1 were obtained from adult pigmented guinea pigs that were either left untreated (vehicle only) or administered a solution containing 10 mM NAC, 10 mM 2,4-DSPBN (HPN-07), and 1 µg/mL Dexamethasone, using cochlear electrode implants with a perfusion and pump system that delivered (intracochlear) the therapeutic at a rate of 1 µL/hour over the course of seven days post-implantation. Animals 12-35 and 12-36 did not receive treatment with 2,4-DSPBN (HPN-07) and NAC after cochlear implantation. Animals 12-37 and 12-39 received 2,4-DSPBN (HPN-07) and NAC after cochlear implantation.

FIG. 2 corresponds to Example 5 and demonstrates that NAC/HPN-07 treatment-mediated attenuation of ABR threshold shifts in a guinea pig model of cochlear implant insertion trauma. The results shown in FIG. 2 were obtained from adult pigmented guinea pigs that were either left untreated or were treated (b.i.d.) with placebo (saline) or a saline solution containing 300 mg/kg of NAC/HPN-07 (i.p.) for two days prior to surgery. A surgical-grade silver wire cochlear electrode mimetic was surgically implanted in one ear of each guinea pig, and animals were either left untreated or were treated with placebo or NAC/HPN-07 (b.i.d.) for seven additional days post-surgery. At three weeks post-surgery, ABR recordings were performed, and ABR thresholds (FIG. 2A) and threshold shifts (FIG. 2B) were measured in placebo (saline) controls and the NHPN-1010-treated animals. FIG. 2A shows that NHPN-1010-specific otoprotection was observed over a broad test frequency range. In placebo treated controls, the insertion trauma consistently induced statistically-significant threshold elevations (, **, $p<0.01$ and $0.001$, respectively) over a broad frequency range (red line) relative to naïve controls (black dashed line). These elevations were significantly attenuated in guinea pigs treated peri-surgically with NAC/HPN-07 across this test range (green line, main effect, ##, $p<0.01$). FIG. 2B shows the calculation of the relative threshold shifts measured in untreated, placebo-treated, or NAC/HPN-07-treated animals revealed a clear trend of broad otoprotection across the entire test frequency range, with statistically-significant protection measured at 16 kHz (*, $p<0.05$).

FIG. 3 corresponds to Example 5 and shows that NAC/HPN-07 treatment significantly-reduced the degree of inner and outer hair cell loss induced by cochlear implant trauma surgery. Adult pigmented guinea pigs were pre-treated (b.i.d.) with either placebo (saline) or a saline solution containing 300 mg/kg of NAC/HPN-07 (i.p.) for two days prior to cochlear implant surgery as described in FIG. 2, followed by post-surgical treatment with either placebo or NAC/HPN-07 (b.i.d.) for seven additional days. At three weeks post-surgery, the animals were euthanized, and cochlear tissues were harvested and fixed for histological evaluations of inner and outer hair cell (IHC and OHC, respectively) loss in whole mount preparations, using a HC-specific antibody (anti-MyoVIIa) and TRITC-conjugated phalloidin to label HC stereocilia. Cochlear HC counts were performed along the aggregate length of each organ of Corti for each specimen, and percent (%) OHC loss, as shown in FIG. 3A, and IHC loss, as shown in FIG. 3B, were averaged and independently graphed as cytocochleograms for both placebo-treated cohorts (triangle shaped data points) and NAC/HPN-07-treated cohorts (circle shaped data points). The numbers above the graphs represent tonotopic frequency positions. In placebo treated controls (triangle shaped data points), the insertion trauma induced pervasive OHC (FIG. 3A) and IHC (FIG. 3B) loss over the 8-32 kHz tonotopic frequency range relative to naïve controls. The extent of this CI surgery-induced HC loss was significantly attenuated in guinea pigs treated peri-surgically with NAC/HPN-07 across this anatomical range (circle shaped data points, main effect, ###, $p<0.001$ in A., ##, $p<0.01$ in B.).

DETAILED DESCRIPTION

It is a surprising discovery of the inventors of the present disclosure that the previously-established synergistic otoprotective properties of NAC and HPN-07 can also protect against hearing loss caused by cochlear implant surgery. Accordingly, the disclosure described herein provides a method for alleviating the negative effects of cochlear electrode implantation. Specific methods of treatment are described herein, but in sum, the method comprises administering an effective amount of 2,4-disulfonyl α-phenyl tertiary butyl nitrone (2,4-DSPBN) and its derivatives or a pharmaceutically acceptable salt thereof (hereinafter referred to as "HPN-07") in combination with N-acetylcysteine and its derivatives or a pharmaceutically acceptable salt thereof (hereinafter referred to as "NAC").

As described in the Examples, a study was conducted to test the effect of HPN-07 and NAC on alleviating hearing loss caused by cochlear implantation surgery. The damage to hearing caused by cochlear implantation can be revealed by performing auditory brainstem response (ABR) testing and measuring loss of hair cells. Most surprisingly, Examples 1 and 5 show that co-administration of HPN-07 and NAC with or without dexamethasone can protect against cochlear implantation-induced hearing loss as determined by ABR measurements and by measuring loss of hair cells. It is a hypothesis of the inventors of the present disclosure that the methods disclosed herein will also provide long-term protection against cochlear implant-induced hearing loss by preventing hair cell loss.

I. Abbreviations 2,4-DSPBN (HPN-07), 2,4-disulfonyl α-phenyl tertiary butyl nitrone; ABR, auditory brainstem response; BHA, butylated hydroxyanisole; BHT, butylated hydroxytoluene; EDTA, ethylenediaminetetraacetic acid; CI, cochlear implant; COX-2, cyclooxygenase-2; dB, decibel; DNA, deoxyribonucleic acid; EIT (electrode insertion trauma); ICAM-1, intercellular adhesion molecule-1; IHC, inner hair cell; IL-1, interleukin-1; iNOS, inducible-nitric oxide synthase; kHz, kilohertz; NAC, N-acetylcysteine; NF-κB, nuclear factor kappaB; OC, the organ of *Corti*; OHC, outer hair cell; RWM, round window membrane; TGF-β, transforming growth factor-beta; TNF-α, tumor necrosis factor-alpha.

II. Methods for Alleviating the Negative Effects of Cochlear Implant Surgery The disclosure herein provides a method for alleviating the negative effects on hearing from cochlear implantation surgery, comprising administering to a subject suffering from negative effects of cochlear implantation an effective amount of HPN-07 or a pharmaceutically acceptable salt thereof and NAC or a pharmaceutically acceptable salt thereof.

During cochlear implantation, an electrode is surgically inserted into the cochlea and connected to auditory nerve fibers, causing trauma to the organs and tissue inside the cochlea. Yawn R. et al. F1000 Prime Report 7, 45 (2015). This trauma to the cochlea inner organs can cause loss of hearing.

Both primary (mechanical) and secondary (molecular) trauma associated with cochlear implant (CI) electrode insertion surgeries contribute to acute and progressive loss of residual hearing acuity. Accordingly, CI surgeries may cause physical or mechanical trauma that contribute to hearing loss.

The study conducted as shown in Example 1 herein demonstrated that administering an effective amount of HPN-07 in combination with NAC can prevent hearing loss caused by cochlear implantation. A combinatorial treatment regimen of NAC and HPN-07 has the potential to address each of these overarching pathological response patterns associated with CI electrode insertion trauma (EIT). Accordingly, in some embodiments, the HPN-07 and NAC are administered to a subject prior to, during, and/or after undergoing cochlear implantation.

The protective effect by HPN-07 and NAC on hearing loss caused by cochlear implantation can be measured by auditory brain stem response (ABR) measurements. ABR is described further below. Briefly, ABR measurements were performed by placing an active needle electrode and a reference electrode proximal to the right ear and the left ear, respectively while a ground electrode was placed at the vertex. Auditory stimuli were generated using a computer-aided system coupled to high frequency transducers. Acoustic stimuli were tone pips at frequencies of 2, 4, 8, 16, and 32 kHz. Hearing thresholds were tested in 10 dB descending steps until near the threshold, and then 5 dB ascending steps were taken to determine the threshold. Threshold was defined as the midpoint between the lowest level of a clear response and the next level where no response was observed. The threshold shift refers to the difference in threshold prior to and following injury, e.g. exposure to a blast, loud sound, ototoxin, etc. Based on ABR measurements, Examples 1 and 5 herein showed that animals that received HPN-07 and NAC together with the cochlear implant were able to detect the test tone at a lower decibel value than control animals. The most pronounced effect of HPN-07 and NAC occurred at the lower 2 and 4 kHz frequencies. Accordingly, the present disclosure provides a method of treating a human subject diagnosed with sensorineural hearing loss prior to, while, and/or after undergoing cochlear implant surgery comprising administering to the subject effective amounts of 2,4-disulfonyl α-phenyl tertiary butyl nitrone (2,4-DSPBN) or a pharmaceutically acceptable salt thereof and N-acetylcysteine (NAC) or a pharmaceutically acceptable salt thereof prior to, during, and/or after undergoing cochlear implant surgery. In some embodiments, the method of treating a human subject diagnosed with sensorineural hearing loss prior to, while, and/or after undergoing cochlear implant surgery further comprises performing auditory brainstem response (ABR) threshold recordings (measured by the sound pressure level in dB required to elicit an ABR response) at one or more test frequencies.

In some embodiments, the method of treating a human subject diagnosed with sensorineural hearing loss prior to, while, and/or after undergoing cochlear implant surgery further comprises comparing an ABR threshold recorded for the subject at the one or more test frequencies to an ABR threshold recorded for an untreated or control subject at the same one or more test frequencies. In some embodiments, the ABR threshold recorded for the subject at the one or more test frequencies is lower compared to that of an untreated or control subject. In some embodiments, the ABR threshold recorded for the subject at the one or more test frequencies is 2-fold, 3-fold, 4-fold, 5-fold, or 10-fold lower compared to that of an untreated or control subject. In some embodiments, the ABR threshold recordings are performed at one or more test frequencies ranging from 1 to 8 kHz.

As used herein, the term "an auditory brainstem response (ABR) threshold" refers to the average of threshold shifts recorded from multiple animals at a given frequency. A threshold shift in this case is the difference in the sound pressure level (dB) required to elicit an ABR response in the original baseline from the sound pressure level required to elicit a response in the same animal after the trauma, in this case the CI surgery. For example, if an animal had a baseline ABR threshold of 25 dB at 8 kHz and a threshold of 75 dB at 8 kHz at three weeks post-CI surgery, then the threshold shift would be 50 dB at that frequency.

It is well-known in the art that test frequencies used in guinea pigs are about 2 fold higher than clinically relevant test frequencies used in human subjects. Accordingly, the test frequencies for guinea pigs of 2, 4, 8, and 16 kHz herein will correspond to the test frequencies 1, 2, 3, or 8 kHz, respectively, in human subjects.

The protective effect of HPN-07 and NAC on hearing loss caused by cochlear implantation was also observed by measuring hair cell loss in Example 5. Accordingly, the present disclosure provides a method of reducing a loss of a plurality of hair cells in a subject prior to, while, and/or after undergoing cochlear implant surgery comprising administering to the human subject effective amounts of 2,4-disulfonyl α-phenyl tertiary butyl nitrone (2,4-DSPBN) or a pharmaceutically acceptable salt thereof and N-acetylcysteine (NAC) or a pharmaceutically acceptable salt thereof prior to, while, and/or after undergoing cochlear implant surgery. In some embodiments, said hair cells comprise inner hair cells, outer hair cells, or both.

In some embodiments, the loss of the plurality of outer hair cells at tonotopic frequency positions ranging from 1 to 8 kHz is reduced by at least about 70% compared that of untreated or control subjects. In some embodiments, the loss of the plurality of outer hair cells at tonotopic frequency positions ranging from 1 to 8 kHz is reduced by at least about 20%, 30%, 40%, 50%, 60%, 70%, 80%, or 90% compared that of untreated or control subjects.

In some embodiments, the loss of the plurality of inner hair cells at tonotopic frequency positions ranging from 1 to 8 kHz is reduced by at least about 38% compared to that of untreated or control subjects. In some embodiments, the loss of the plurality of inner hair cells at tonotopic frequency positions ranging from 1 to 8 kHz is reduced by at least about 20%, 30%, 40%, 50%, 60%, 70%, 80%, or 90% compared that of untreated or control subjects.

In some embodiments, the loss of the plurality of outer hair cells at tonotopic frequency positions ranging from 2 to 8 kHz is reduced by at least about 86% compared to that of untreated or control subjects. In some embodiments, the loss of the plurality of outer hair cells at tonotopic frequency positions ranging from 1 to 8 kHz is reduced by at least about 20%, 30%, 40%, 50%, 60%, 70%, 80%, or 90% compared that of untreated or control subjects.

In some embodiments, the loss of the plurality of inner hair cells at tonotopic frequency positions ranging from 2 to 8 kHz is reduced by at least about 64% compared to that of untreated or control subjects. In some embodiments, the loss of the plurality of inner hair cells at tonotopic frequency positions ranging from 1 to 8 kHz is reduced by at least about 20%, 30%, 40%, 50%, 60%, 70%, 80%, or 90% compared that of untreated or control subjects.

Without being bound by theory, it is a hypothesis of the present disclosure that HPN-07 and/or NAC may prevent hearing loss by preventing oxidative stress, inflammation, and cell death. Accordingly, the protective effect of HPN-07 and NAC on hearing loss caused by cochlear implantation may also be observed by histological evaluation of biomarkers for oxidative stress, inflammation, and/or cell death pathways as further described below.

NAC may target oxidative stress, glutathione deficiency, neuroinflammation, mitochondrial injury and caspase-mediated (apoptotic) cell death (Kopke et al., *Hear Res.* 226(1-2):114-25 (2007)). NAC may serve directly as a potent scavenger of reactive oxygen species (through nucleophilic interactions), such as $H_2O_2$ and OH. Importantly, NAC may also act as an antioxidant by serving as a precursor of cysteine, the rate-limiting metabolite in glutathione synthesis. Glutathione, in turn, reduces hydroperoxides catalyzed by glutathione peroxidases and by conjugation reactions that are catalyzed by glutathione-S-transferases, processes that are essential for the body's intrinsic antioxidant and anti-apoptotic defense systems (Dodd et al., *Expert Opin. Biol. Ther.* 8(12):1955-1962 (2008); Franco and Cidlowski, *Cell Death and Differentiation* 16: 1303-1314 (2009)).

NAC may also have potent anti-inflammatory properties by significantly limiting the induction of pro-inflammatory transcription factors, such as the nuclear factor kappaB (NF-κB) (Shahripour et al., *Brain and Behavior* 4(2): 108-122 (2014)). Furthermore, NAC may block or attenuate a myriad of other stress-induced pro-inflammatory and pro-apoptotic modulators, including TNFα, interleukin-1 (IL-1), cyclooxygenase-2 (COX-2), intercellular adhesion molecule-1 (ICAM-1), and Caspase 3 ((Chen et al., *Mediators Inflamm.* 2008:716458 (2008); Lindblad, *Noise Health.* 13(55):392-401 (2011); Kopke et al., *Hear Res.* 323:40-50 (2015)).

Moreover, NAC may inhibit proliferative fibrosis and transforming growth factor-beta (TGF-β) activity (Sugiura et al., *Pulm Pharmacol Ther.* 22(6): 487-91 (2009); Li et al., *Respiration* 84(6): 509-17 (2012); Shen et al., *Acta Pharmacol Sin.* 37(5): 637-44 (2016) and, more specifically, NAC may reduce cochlear fibrosis and ossification in rodent meningitis models (Klein et al., *Ann Neurol.* 54(4):451-8 (2003); Wilk et al., *PLoS One* 11(2): e0147552 (2016)).

HPN-07 or 2,4-disulfonyl α-phenyl tertiary butyl nitrone (2,4-DSPBN) may function to scavenge and neutralize free radicals to generate nitroxide conjugates that are stable and readily excreted from the body (Williams et al., *Free Radic. Res.* 41:1047-52(2007)). HPN-07 may reduce glutamate excitotoxicity by direct and indirect inhibition of inducible-nitric oxide synthase (iNOS), COX-2, and NF-kB (Floyd et al., *Anticancer Agents Med Chem.* 1; 11(4): 373-379 (2011)). Without being bound by theory, it is an hypothesis herein that suppression of iNOS expression by HPN-07 may, in part, be due to the capacity of HPN-07 to inhibit stress-induced NF-κB DNA binding (Kotake et al., *Biochim Biophys Acta.* 1448:77-84 (1998)) and may be extended to direct and indirect inhibition of a variety of other pro-inflammatory pathways.

Accordingly, useful biomarkers for histological evaluation of the effects of NAC and HPN-07 on stress-induced inflammation and cell death may include but are not limited to TNFα, interleukin-1 (IL-1), cyclooxygenase-2 (COX-2), NF-κB DNA binding, intercellular adhesion molecule-1 (ICAM-1), Caspase 3, and TGF-β.

A. 2,4-Disulfonyl α-Phenyl Tertiary Butyl Nitrone (2,4-DSPBN or HPN-07)

2,4-disulfonyl α-phenyl tertiary butyl nitrone is also referred to as 2,4-disulfonyl PBN, 2,4-DSPBN, NXY-059 or HPN-07. It has the following structure:

The acid form of the compound has the following structure:

The acid form may be a solid or found in low pH solutions. The ionized salt form of the compound exists at higher pH and may be represented by either of the following structures:

In the salt form, X is a pharmaceutically acceptable cation. Most commonly, this cation is a monovalent material such as sodium, potassium or ammonium, but it can also be a multivalent alone or cation in combination with a pharmaceutically acceptable monovalent anion, for example calcium with a chloride, bromide, iodide, hydroxyl, nitrate, sulfonate, acetate, tartrate, oxalate, succinate, pamoate or the like anion; magnesium with such anions; zinc with such anions or the like. Among these materials, the free acid and the simple sodium, potassium or ammonium salts are most preferred with the calcium and magnesium salts also being preferred but somewhat less so. 2,4-DSPBN is described in detail by U.S. Pat. No. 5,488,145, which is incorporated herein by reference. The salts of 2,4-DSPBN may also be used for alleviating hearing loss caused by cochlear implantation in a manner similar to the use of 2,4-DSPBN as described herein.

The 2,4-DSPBN or pharmaceutically acceptable salt thereof may be present in the modified release dosage form in a pharmaceutically acceptable amount, or a portion thereof, for example 50% of a pharmaceutically acceptable amount when the modified release dosage form is intended to be dosed at two capsules. For example, in some embodiments, the 2,4-DSPBN or pharmaceutically acceptable salt thereof is contained in the modified release dosage form in an amount of from about 250 mg to about 3000 mg. For example, some embodiments include about 250, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 mg, and values or ranges therein between, 2,4-DSPBN or pharmaceutically acceptable salt. In some embodiments, this weight of 2,4-DSPBN or pharmaceutically acceptable salt thereof is based on the weight of 2,4-DSPBN moiety so that the counter-ion of a pharmaceutically acceptable salt does not affect the molar amount of 2,4-DSPBN.

To alleviate the negative effects on hearing of cochlear implantation, 2,4-DSPBN can be administered at a dose of, for example, between about 1 mg/kg to about 1000 mg/kg body weight, between about 50 mg/kg to about 800 mg/kg body weight, between about 100 mg/kg to about 600 mg/kg body weight, between about 200 mg/kg to about 400.

In some embodiments the dosage of 2,4-DSPBN may be about 50 mg/kg body weight, about 100 mg/kg body weight, about 200 mg/kg body weight, about 300 mg/kg body weight, about 400 mg/kg body weight, about 500 mg/kg body weight, about 600 mg/kg body weight, about 700 mg/kg body weight, about 800 mg/kg body weight, about 900 mg/kg body weight, or about 1000 mg/kg body weight.

To alleviate the negative effects on hearing of cochlear implantation in a human subject, 2,4-DSPBN can be administered at a daily dose of, for example, between about 100 mg to about 20,000 mg, or between about 500 mg to about 10,000 mg, or between about 1,000 mg to about 5,000 mg, or at about 100 mg, or at about 200 mg, or at about 500 mg, or at about 1,000 mg, or at about 2,000 mg, or at about 3,000 mg, or at about 5,000 mg, or at about 8,000 mg, or at about 10,000 mg.

The subject can be administered one dose daily, or two doses daily, or three doses daily, or four doses daily, or five doses daily.

B. N-Acetylcysteine (NAC)

In some embodiments, the NAC is an isomerically pure or enriched (e.g., 95, 96, 97, 98, 99, 99.5, 99.9 enantiomeric excess, defined as the absolute difference between the mole fraction of each enantiomer) form of N-acetyl-L-cysteine. In some embodiments, the NAC is a racemic mixture of N-acetylcysteine.

To alleviate the negative effects on hearing of cochlear implantation, NAC may be administered at a dose of, for example, between about 1 mg/kg to about 1000 mg/kg body weight, between about 50 mg/kg to about 800 mg/kg body weight, between about 100 mg/kg to about 600 mg/kg body weight, between about 200 mg/kg to about 400.

In some embodiments the dosage of NAC may be about 50 mg/kg body weight, about 100 mg/kg body weight, about 200 mg/kg body weight, about 300 mg/kg body weight, about 400 mg/kg body weight, about 500 mg/kg body weight, about 600 mg/kg body weight, about 700 mg/kg body weight, about 800 mg/kg body weight, about 900 mg/kg body weight, or about 1000 mg/kg body weight.

To alleviate the negative effects on hearing of cochlear implantation in a human subject, NAC may be administered at a daily dose of, for example, between about 100 mg to about 20,000 mg, or between about 500 mg to about 10,000 mg, or between about 1,000 mg to about 5,000 mg, or at about 100 mg, or at about 200 mg, or at about 500 mg, or at about 1,000 mg, or at about 2,000 mg, or at about 3,000 mg, or at about 5,000 mg, or at about 8,000 mg, or at about 10,000 mg.

In some embodiments, the modified release dosage form comprises a plurality of pellets of NAC or the pharmaceutically acceptable salt thereof. The pellets may be, for example a target size 0.5 mm up to a target size of 2.5 mm+10% with no pellets over that 2.8 mm.

The NAC or a pharmaceutically acceptable salt thereof may be present in the modified release dosage form in a pharmaceutically acceptable amount, or a portion thereof, for example 50% of a pharmaceutically acceptable amount when the modified release dosage form is intended to be dosed at two capsules or tablets (e.g., compressed tablets). For example, in some embodiments, the NAC or pharmaceutically acceptable salt thereof is contained in the modified release dosage form in an amount of from about 300 mg to about 2400 mg. For example, some embodiments include about 300, 400, 500, 600, 700, 800, 900, 1000, 1100, 1200, 1300, 1400, 1500, 1600, 1700, 1800, 1900, 2000, 2100, 2200, 2300, or 2400, and values or ranges therein between mg NAC. In some embodiments, this weight of NAC or pharmaceutically acceptable salt thereof is based on the weight of N-acetylcysteine moiety so that the counter-ion of a pharmaceutically acceptable salt does not affect the molar amount of NAC.

C. Routes of Administration

The route of administration of HPN-07 and NAC may also influence the protective effect against cochlear implant-induced hearing loss. In some embodiments, of HPN-07 and NAC are co-administered as a mixture. In some embodiments, of HPN-07 and NAC are administered sequentially or simultaneously as distinct dosage forms.

In one aspect, the effective dose of HPN-07 and NAC may be administered locally directly into the cochlea. In one embodiment, the effective dose of HPN-07 and NAC may be delivered intra-tympanically. For example, the effective dose of HPN-07 and NAC may be delivered directly into the middle ear by injection through the tympanic membrane. Alternatively, the active composition may be administered by coating an electrode with the composition prior to the electrode is implanted in the subject undergoing cochlear implantation. Further, the active composition may be administered as a nanoparticle or dendrimer formulation. The nanoparticle may be multifunctional and composed of a polymer and paramagnetic iron oxide particles to allow the application of external magnetic forces to aid in the delivery of the drug to the desired target such as the inner ear.

In one embodiment, of HPN-07 and NAC may be delivered indirectly to the round window membrane (RWM) of the middle ear. It has been shown that RWM functions as a semipermeable membrane that will allow many substances, particularly low molecular weight substances, to penetrate to the inner ear when applied to the RWM of the middle ear. See, e.g., Duan et al., Journal of Otology, 4(1): 34-43 (2009).

In another aspect, the effective dose of HPN-07 and NAC may be administered systemically. Systemic administration may be performed orally, intranasally, or by injection. Administering via injection may be performed intraperitoneally, intravenously, or intramuscularly. Other delivery methods include, but are not limited to, inhalation, sublingually, subdermally, or intrathecally.

In one aspect, the administration of HPN-07 and NAC may be performed prior to, during, or following the cochlear implantation surgery.

In another aspect, the administration of HPN-07 and NAC may be performed prior to, during, and following the cochlear implantation surgery. In some embodiments, HPN-07 and NAC may be administered orally prior to, during, and after the surgery. In some embodiments, HPN-07 and NAC may be administered intravenously or topically prior to the surgery, and orally during or after the surgery. In some embodiments, HPN-07 and NAC may be administered orally prior to the surgery, intravenously at the time or immediately prior to the surgery, and orally after the surgery.

In some embodiments, the HPN-07 or its pharmaceutically acceptable salt and NAC are administered to the subject for at least one month, at least three months, at least six months, at least one year, or at least two years, after the cochlear implantation.

In some embodiments, the HPN-07 or its pharmaceutically acceptable salt and the NAC are administered to a subject who has suffered from negative effects of cochlear implantation for at least one month, at least three months, at least six months, at least one year, or at least two years.

D. Subject Populations

The disclosed compositions can be used to treat a wide range of human subjects. In some embodiments, the human subject to be treated may belong to an adult population.

In some embodiments, the human subject to be treated may belong to a pediatric population. As used herein the term "pediatric population" refers to a population of neonates (birth to 1 month), infants (1 month to 2 years), developing children (2-12 years), and adolescents (12-16 years). Accordingly, any subject within the age range of birth to 16 years will belong to a pediatric population. A subject older than 16 years will belong to an adult population.

E. Composition Components

In some embodiments, a pharmaceutical composition disclosed herein comprises one or more pharmaceutically acceptable carriers, such as an aqueous carrier, buffer, and/or diluent.

In some embodiments, a pharmaceutical composition disclosed herein further comprises a simple polyol compound, such as glycerin. Other examples of polyol compounds include sugar alcohols. In some embodiments, a pharmaceutical composition disclosed herein comprises an aqueous carrier and glycerin at about a 2:1 ratio.

The formulations may conveniently be presented in unit dosage form and may be prepared by any of the methods well known in the art of pharmacy. An exemplary oral dosage form is a tablet or capsule. An exemplary intranasal dosage form is a liquid or powder nasal spray. A nasal spray is designed to deliver drug to the upper nasal cavity, and can be a liquid or powder formulation, and in a dosage form such as an aerosol, liquid spray, or powder.

The HPN-07 and/or NAC may be combined or coordinately administered with a suitable carrier or vehicle depending on the route of administration. As used herein, the term "carrier" means a pharmaceutically acceptable solid or liquid filler, diluent or encapsulating material. A water-containing liquid carrier can comprise pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857-1859, and (1990). Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Any pharmaceutical used for therapeutic administration can be sterile. Sterility is readily accomplished by for example filtration through sterile filtration membranes (e.g., 0.2 micron membranes). Any pharmaceutically acceptable sterility method can be used in the compositions of the invention.

The pharmaceutical composition comprising HPN-07 derivatives or salts thereof or a NAC derivatives or salts thereof will be formulated and dosed in a fashion consistent with good medical practice, taking into account the clinical condition of the individual patient, the method of administration, the scheduling of administration, and other factors known to practitioners.

F. Kits

HPN-07, NAC, and/or combination of HPN-07 and NAC formulations or compositions of the invention may be packaged together or included in a kit along with instructions or a package insert. Such instructions or package inserts may address recommended storage conditions, such as time, temperature and light, taking into account the shelf-life of the HPN-07 or derivatives or salts thereof, and the NAC or derivatives or salts thereof. Such instructions or package inserts may also address the particular advantages of the HPN-07 or derivatives or salts thereof, and the NAC or derivatives or salts thereof, such as the ease of storage for formulations that may require use in the field, outside of controlled hospital, clinic or office conditions.

The invention also provides a pharmaceutical pack or kit comprising one or more containers filled with one or more HPN-07 and/or NAC pharmaceutical compositions disclosed herein. The kits may include, for instance, containers filled with an appropriate amount of an HPN-07 and/or NAC pharmaceutical composition, either as a powder, a tablet, to be dissolved, or as a sterile solution. Associated with such container(s) can be a notice in the form prescribed by a governmental agency regulating the manufacture, use or sale of pharmaceuticals or biological products, which notice reflects approval by the agency of manufacture, use or sale for human administration. In addition, the HPN-07 and/or NAC may be employed in conjunction with other therapeutic compounds.

In other aspects, a kit comprising a nasal spray device as described herein is disclosed. In one aspect, the kit may comprise one or more devices as disclosed herein, comprising a disclosed low dose HPN-07 and/or NAC composition, wherein the device is sealed within a container sufficient to protect the device from atmospheric influences. The container may be, for example, a foil, or plastic pouch, particularly a foil pouch, or heat-sealed foil pouch. Suitable containers sufficient to adequately protect the device will be readily appreciated by one of skill in the art.

In one aspect, the kit may comprise one or more devices as disclosed herein, wherein the device may be sealed within a first protective packaging, or a second protective packaging, or a third protective packaging, that protects the physical integrity of the product. One or more of the first, second, or third protective packaging may comprise a foil pouch. The kit may further comprise instructions for use of the device. In one aspect, the kit contains two or more devices.

In one aspect, the kit may comprise a device as disclosed herein, and may further comprise instructions for use. In one aspect, the instructions may comprise visual aid/pictorial and/or written directions to an administrator of the device.

III. Definitions

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the phrase "effective amount" shall mean the drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

The term "administering" as used herein includes prescribing for administration as well as actually administering and includes physically administering by the subject being treated or by another.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

The terms "treatment," "treating," or any variation thereof includes reducing, ameliorating, or eliminating (i) one or more specified symptoms and/or (ii) one or more symptoms or effects of a specified disorder. The terms "prevention," "preventing," or any variation thereof includes reducing, ameliorating, or eliminating the risk of developing (i) one or more specified symptoms and/or (ii) one or more symptoms or effects of a specified disorder.

IV. Equivalents

It is to be understood that while the disclosure has been described in conjunction with the above embodiments, the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs.

The embodiments illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement, and variation of the embodiments therein herein disclosed may be resorted to by those skilled in the art, and that such modifications, improvements, and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

EXAMPLES

Method of Performing Auditory Brainstem Response

Hearing was assessed using auditory brainstem responses (ABRs) which were measured at between 1 and 3 days prior to AAT and at one or more of the following time points post AAT: 1 hr, 8 hr, 24 hr, 7 day and 21 days. The ABR threshold shift at the 21-day test point was considered to be the permanent threshold shift (PTS). ABR recordings were performed under ketamine (90 mg/kg) and xylazine (9 mg/kg) anesthesia. Small supplemental doses (⅓ of initial dose) of anesthesia were given if needed. ABRs were recorded via subcutaneous needle electrodes placed on the scalp, where the active electrode was located at the vertex, while the reference and ground electrodes were placed at the ipsilateral and contralateral mastoid, respectively. The electrical responses obtained from the electrodes were amplified (×100,000), filtered (100-3,000 Hz), and digitized on a signal processing board. They were averaged across 1024 repetitions at a rate of 21/s for each stimulus level. Acoustic stimuli were tone bursts of alternating polarity with 5-ms plateau and 0.5-ms cos 2 rise-fall envelope at frequencies of 2, 4, 8, 16, and 32 kHz. The stimuli were delivered through a high frequency transducer whose end was fitted with a rubber tip sealing the ear canal. The transducer was calibrated by using a coupler cavity of equivalent volume to that of an adult subject ear, which was mounted to a sound level meter. Stimulus generation and data acquisition were accomplished using a computer-aided SmartEP (Intelligent Hearing Systems, Miami, Fla.).

Hearing thresholds were tested in 10 dB descending steps until near the threshold, and then 5 dB ascending steps were taken to determine the threshold. Threshold was defined as the midpoint between the lowest level of a clear response and the next level where no response was observed. The threshold shift refers to the difference in threshold prior to and following AAT. The investigators performing the ABR measurements were blinded as to the identity of the animal groups.

Example 1

The purpose of this example was to demonstrate that a composition comprising 2,4-disulfonyl PBN (HPN-07), N-acetylcysteine (NAC), and dexamethasone can alleviate hearing loss induced by cochlear implant trauma in guinea pigs.

Surgical procedure. For this experiment, one ear was implanted with a guinea pig silicone cochlear electrode and a mini-osmotic pump device. First, general anesthesia was obtained by a mixture of xylazine and ketamine completed with subcutaneous injection of xylocaine at the time of skin incision and mini-pump placement. Then, the retroauricular area was shaved and sterilized with iodine and 70% alcohol. A retroauricular approach was used to expose the bulla and the vertex. The bulla opening was then drilled with a 2 mm diamond burr to expose the round window and the basal turn of the cochlea. The cochleostomy was then performed 1-2 mm under the round window niche using a 0.5 mm diamond burr until perilymph was visualized. The silicone electrode was then inserted 3 mm into the scala tympani using a microforceps. A small muscle graft (about 1×1 mm) taken from sternocleidomastoid muscle was packed around the electrode carrier and a drop of 2-octyl cyanoacrylate (Dermabond, Ethicon) was used to prevent any inner ear fluid leak. The wound was completely sutured in two layers.

Table 1 below shows the treatment protocol for this example. The two guinea pigs in test group T-1 were implanted with delivery vehicle only (artificial perilymph). Two guinea pigs were implanted with active treatment agents of HPN07 (10 mM)+NAC (10 mM)+dexamethasone (1 μg/ml) in artificial perilymph designated test group T-2. Animals in group C were the normal control group, having no cochlear implant surgery performed. Table 2 lists the results for the effect on hearing as auditory brainstem response at 2 kHz, 4 kHz, 8 kHz, and 16 kHz immediately and 4 weeks after the cochlear implant surgeries were performed. Table 3 shows ABR results from the normal guinea pigs.

TABLE 1

Treatment protocol for testing the effect of HPN-07 and NAC on treating hearing loss because of cochlear implants.

| Test Group | Animal ID | Treatment Protocol for the Left Ear |
|---|---|---|
| T-1 | GP 12-35<br>GP 12-36 | Cochlear Implant |
| T-2 | GP 12-37<br>GP 12-39 | Cochlear Implant with NAC and HPN-07 |
| C | GP 12-34<br>GP 12-38 | Normal Control |

TABLE 2

ABR measurements for testing the effect of HPN-07 and NAC on hearing loss caused by cochlear implants.

| | | Animal ID | | | | | | | | | | | | | | | |
|---|---|---|---|---|---|---|---|---|---|---|---|---|---|---|---|---|---|
| | | GP 12-35 | | | | GP 12-36 | | | | GP 12-37 | | | | GP 12-39 | | | |
| Time Point | Ear | 2 kHz | 4 kHz | 8 kHz | 16 kHz | 2 kHz | 4 kHz | 8 kHz | 16 kHz | 2 kHz | 4 kHz | 8 kHz | 16 kHz | 2 kHz | 4 kHz | 8 kHz | 16 kHz |
| Baseline | L | 30 | 25 | 25 | 30 | 35 | 35 | 30 | 35 | 35 | 25 | 25 | 35 | 35 | 25 | 25 | 30 |
| | R | 30 | 25 | 20 | 30 | 40 | 30 | 25 | 30 | 25 | 20 | 25 | 30 | 40 | 25 | 35 | 35 |
| Immediately | L | 80 | 75 | 70 | 85 | 75 | 75 | 75 | 80 | 65 | 55 | 60 | 70 | 60 | 45 | 55 | 80 |
| | R | 30 | 40 | 30 | 35 | 40 | 35 | 30 | 35 | 25 | 20 | 25 | 30 | 40 | 25 | 35 | 35 |
| Week 4 | L | 80 | 90 | 100 | 101 | 60 | 85 | 95 | 101 | 50 | 40 | 90 | 101 | 40 | 40 | 70 | 80 |
| | R | 30 | 25 | 25 | 30 | 40 | 30 | 25 | 30 | 25 | 25 | 25 | 30 | 40 | 30 | 35 | 35 |

Table 3 shows ABR results from the normal guinea pigs.

| | | Animal ID | | | | | | | |
|---|---|---|---|---|---|---|---|---|---|
| | | GP 12-34 | | | | GP 12-38 | | | |
| Time Point | Ear | 2 kHz | 4 kHz | 8 kHz | 16 kHz | 2 kHz | 4 kHz | 8 kHz | 16 kHz |
| Baseline | L | 35 | 25 | 25 | 20 | 30 | 35 | 35 | 35 |
| | R | 40 | 40 | 35 | 35 | 40 | 45 | 40 | 40 |
| Week 4 | L | 35 | 25 | 25 | 20 | 30 | 35 | 35 | 35 |
| | R | 40 | 40 | 35 | 35 | 40 | 45 | 40 | 40 |

Figure 1:
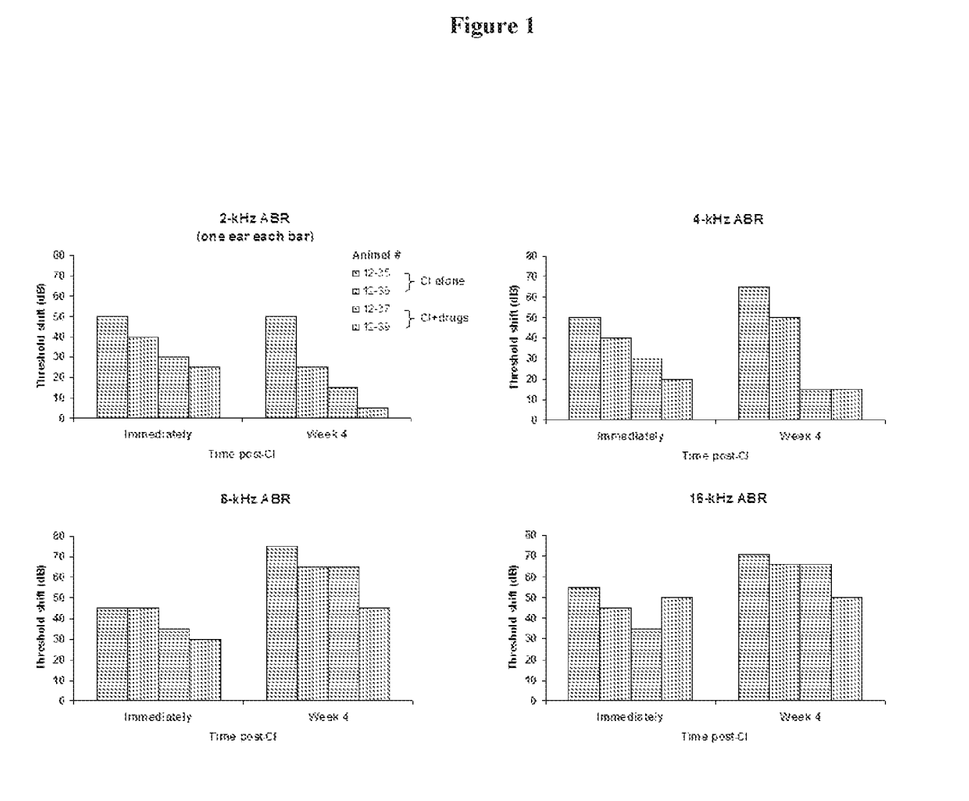

FIG. 1 shows threshold values across all tested frequencies compared to control animals. As demonstrated in FIG. 1, the most pronounced effect of HPN-07/NAC/Dexamethasone treatment occurred at 2 and 4 kHz. This suggests that animals receiving HPN-07/NAC/Dexamethasone treatment were able to detect the test tone at a lower decibel value than control animals.

Example 2

The purpose of this example is to determine the impact of NAC and HPN-07 on animals with cochlear implants. The experimental protocol is shown in Table 4 below.

TABLE 4

Experimental setup to determine the short term impact of NAC

| Group (n = 6/group) | Intervention 1 | Intervention 2 | Measurement | Outcome |
|---|---|---|---|---|
| 1. Control | No surgery | None | ABR and histology | Effect of implant w/o treatment on cochlear histology and function |
| 2. Experimental | Implant | vehicle | | |
| 3. Experimental | Implant | NAC + HPN07 Dosed IP pre and post surgery and treated twice daily for 2 weeks | | |

As shown in Table 4, three groups of animals are compared. Group 1 includes control animals undergoing no surgery. Group 2 includes animals having cochlear implant surgery performed but untreated. Group 3 includes animals having cochlear implant surgery performed and treated with HPN-07 and NAC by intraperitoneal injection both pre- and post-surgery, twice daily for 2 weeks. The animals will be observed for four weeks post implantation.

The animals are treated with 300 mg/kg of HPN-07 and 300 mg/kg of NAC. This dosage may be increased to 600 mg/kg for each drug.

The effect of HPN-07 and NAC are measured by ABR and by hair cell loss as determined by histological analysis at 4 weeks post implantation.

Example 3

The purpose of this example is to determine the long-term impact of NAC and HPN-07 on animals with cochlear implants. This experiment aims to define the time course of the injury caused by cochlear implants, and to determine the cellular mechanisms associated with cochlear insertion trauma. Both early and delayed effects of cochlear implantation are investigated.

The experimental design is to perform cochlear implantation in one ear of the animals and evaluate their hearing over time compared to control animals with no surgery and in side by side comparison between untreated animals and animals treated with HPN-07 and NAC as shown in table 5 below. Hearing loss was assessed in the animals at 48 hours, 10 days, 8 weeks, and 12 weeks after cochlear implantation. Hearing loss is determined by ABR analysis. Histological analysis is performed to measure hair cell and spiral ganglion neuron counts. In addition, histological analysis is performed to measure biomarkers for oxidative stress, inflammation, and cell death pathways.

TABLE 5

Study protocol of evaluating long-term effect of NAC and HPN-07 over 12 weeks post-surgery

| Group | Intervention | Time interval | | | | Measurement | Outcome |
|---|---|---|---|---|---|---|---|
| 1. Control | No surgery | 48 h | 10 d | 8 w | 12 w | ABR and histology (8 and 12 weeks) | Long term effect of implant w/wo treatment on cochlear structure and function |
| 2. Experimental | Implant + vehicle | 48 h | 10 d | 8 w | 12 w | | |
| 3. Experimental | Implant with NAC + HPN07 treatment | 48 h | 10 d | 8 w | 12 w | | |

Example 4

The purpose of this example is to determine the impact of mode of delivery of NAC and HPN-07 (the combination of NAC and HPN-07 is sometimes referred to as NHPN-1010) on hearing loss caused by cochlear implantation.

This experiment compares the effect of administering NAC and HPN-07 by systemic routes with intraperitoneal injection, by local delivery via round window membrane (RWM), by intracochlear routes, and by elution from an electrode as shown in Table 6 below. The experimental animals only have one ear implanted and treated. Each treatment group has an inactive vehicle control and may have a mock control as appropriate. The long-term effect of NAC and HPN-07 on cochlear implant induced hearing loss is measured throughout the treatment period by ABR and by histological analysis of hair cell loss.

TABLE 6

Experimental protocol for comparing 4 different modes of administering HPN-07 and NAC

| Mode of delivery | Time interval | | | | Measurement | Outcome |
|---|---|---|---|---|---|---|
| Systemic (IP) | 48 h or 2 wk | 4 wk | 8 wk | 12 wk | ABR (48 h or 2 weeks?), 4, 8, and 12 weeks. | Determine the effect of mode of NAC and HPN-07 treatment delivery for optimal mitigation of implant trauma. |
| RWM | 48 h or 2 wk | 4 wk | 8 wk | 12 wk | | |
| Intracochlear | 48 h or 2 wk | 4 wk | 8 wk | 12 wk | | |
| Elution from electrode | 48 h or 2 wk | 4 wk | 8 wk | 12 wk | | |

Example 5

The purpose of this example was to evaluate the predicted protective effects of NAC and HPN-07 against cochlear electrode implantation-induced auditory brainstem response (ABR) threshold elevations and hair cell loss in a pilot study conducted in adult pigmented guinea pigs.

Experimental Design

To measure post-operative ABR threshold shifts, baseline ABR recordings were performed on all guinea pigs in the study prior to initiating experimentation. The guinea pigs were then either left untreated or were pre-treated (b.i.d.) with either placebo (saline) or a saline solution containing 300 mg/kg (each) of NAC and HPN-07 (i.p.) for two days prior to surgery. Silver wire (0.0055") coated with perfluoroalkoxy alkane (PFA) was used to make the electrode mimetic (A-M System Inc, Carlsborg, WA). The end intended for implantation was melted into a ball (300-400 um) using a propane/oxygen torch. On the day of surgery, the surgical-grade silver wire cochlear electrode mimetic was surgically implanted in one ear of each guinea pig. A retroauricular approach was used to surgically expose the bulla and the vertex. The bullar opening was then drilled with a 2 mm diamond burr to expose the round window and the basal turn of the cochlea. The cochleostomy was then performed 1-2 mm under the round window niche using a 0.5 mm diamond burr until perilymph was visualized. The silver wire was then inserted approximately 3.5-4 mm into the scala tympani using micro-forceps. A small muscle graft (about 1×1 mm) taken from sternocleidomastoid muscle was packed around the electrode carrier. The wire was hold onto the bulla by using dental cement. The wound was completely sutured in two layers.

On the day of surgery, animals were either left untreated or were post-operatively administered (i.p.) a single dose of NAC/HPN-07 (300 mg/kg of each) or an equivalent volume of saline (placebo) solution. Animals were then either left untreated or were treated with NAC/HPN-07 (b.i.d.) or saline for an additional seven days. At three weeks post-surgery, terminal ABR recordings were performed, and threshold shifts were measured for each animal in each experimental cohort. The animals were then euthanized, and cochlear tissues were harvested and fixed for histological evaluations of inner and outer hair cell (IHC and OHC, respectively) loss in whole mount preparations, using a HC-specific antibody (anti-MyoVIIa).

Results

Figure 2:
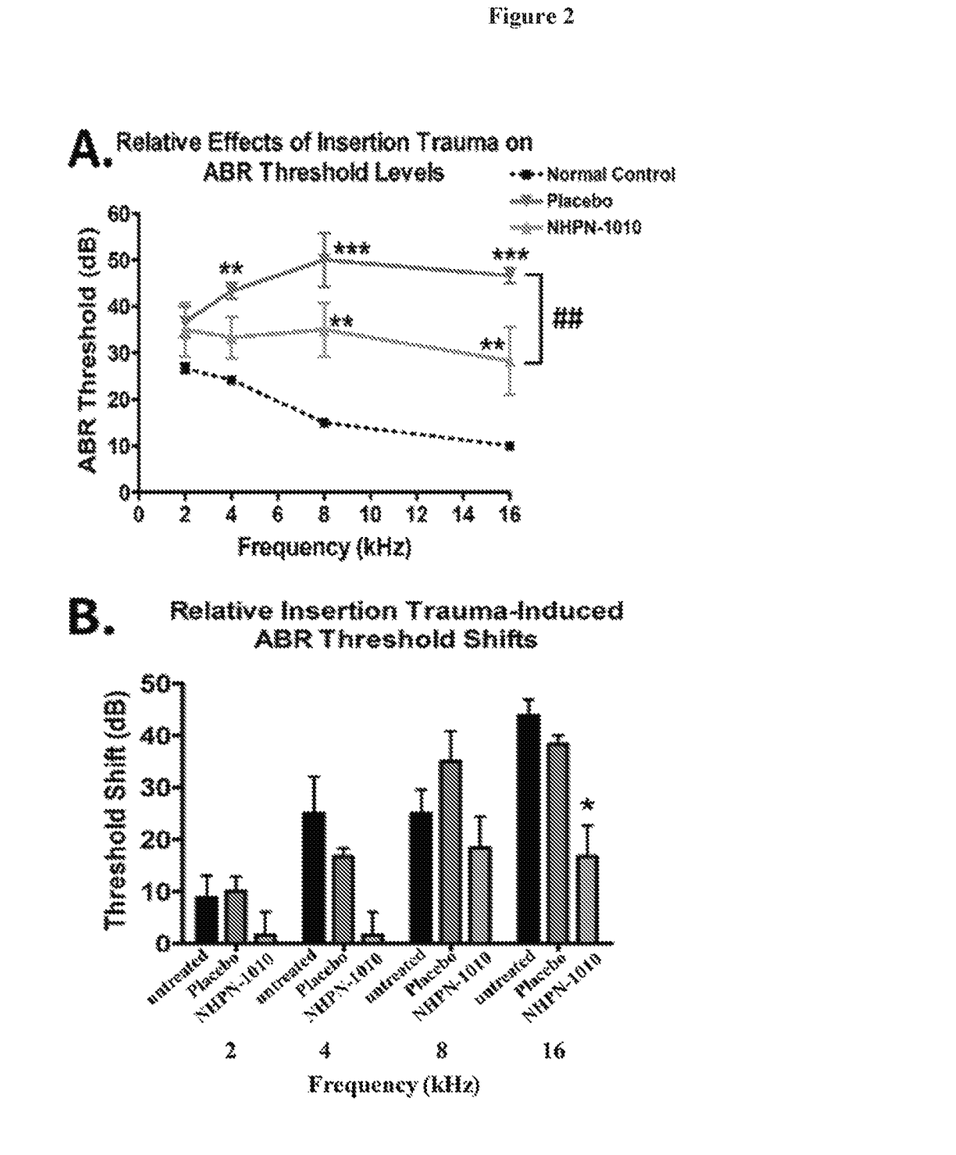

As summarized in FIG. 2A, at three weeks post-surgery, ABR thresholds were significantly elevated (10-40 dB) across a broad frequency range in guinea pig *cochleae* that were implanted with the cochlear electrode mimetic and treated with placebo, with the gradation of hearing loss occurring in an apical-to-basal (low-to-high frequency) manner. The average ABR threshold shift (25.0 dB relative to pre-surgery levels) across the 2-16 kHz frequency range in these animals was similar to that measured for untreated controls (25.6 DB) that were surgically-implanted in the same manner but were treated with neither placebo or NAC/HPN-07 as shown in FIG. 2B. However, in surgically-implanted *cochleae* from guinea pigs peri-surgically treated with NAC/HPN-07, the average ABR thresholds were significantly lower (FIG. 2A, main effect, $p<0.01$) across the same test frequency range, resulting in a markedly-reduced average threshold shift (10.4 dB), indicative of a sustained, treatment-specific otoprotective effect. Although the number of animals in this study was small (n=3 per group), the NAC/HPN-07-specific sparing of hearing function over a broad test frequency range was clear, with three-fold reduced average threshold shifts at the 2 and 4 kHz test frequencies and a statistically-significant reduction in ABR threshold shift at 16 kHz that represented a more than two-fold lower sensitivity threshold than that measured in either placebo or untreated controls.

Figure 3:
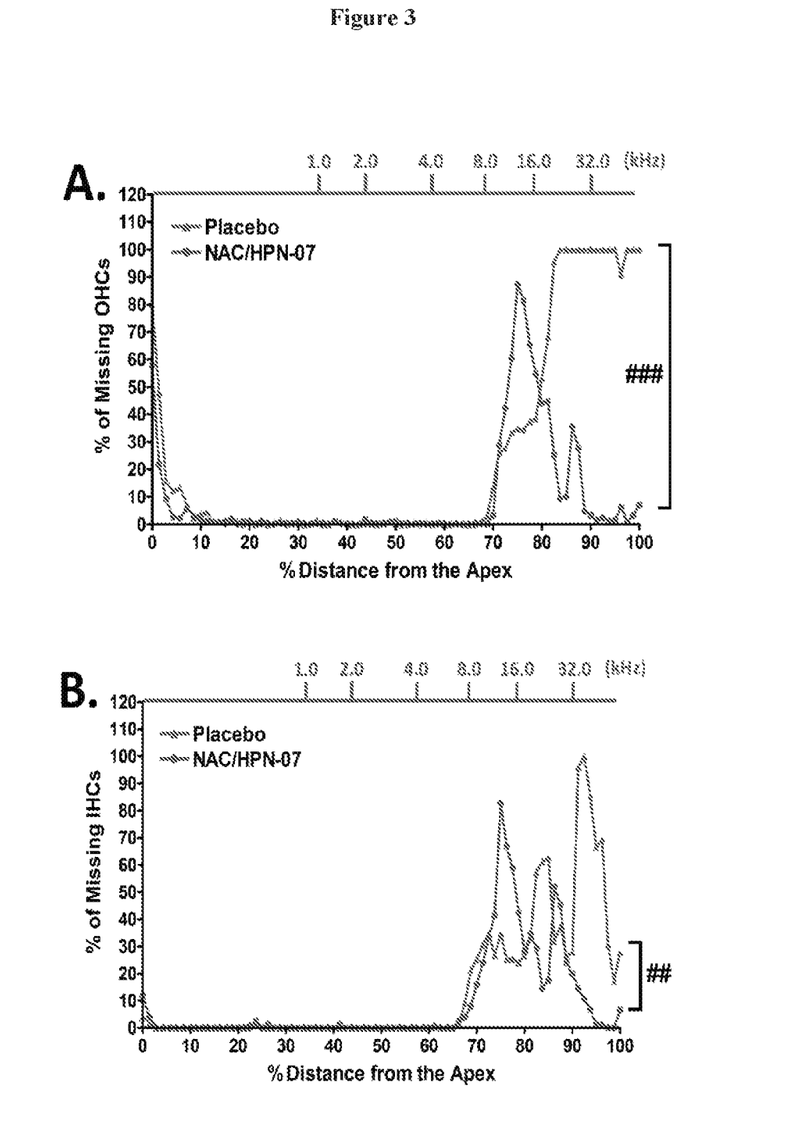

As shown in the cytocochleograms in FIG. 3, significant outer hair cell (OHC) and inner hair cell (IHC) losses were measured in untreated and placebo-treated ears at three-weeks after cochlear electrode implantation surgery, with the majority of the losses occurring across the 8-32 kHz tonotopic frequency positions. Among the guinea pigs treated peri-surgically with NAC/HPN-07, the relative sizes of the lesions across this tonotopic span were dramatically reduced, resulting in a statistically-significant treatment effect (main effect, ###, $p<0.001$ for OHCs and ##, $p<0.01$ for IHCs). Remarkably, across the tonotopic frequency positions corresponding to 8-32 kHz, the average CI-surgery-related OHC loss was reduced from 85.1 (±3.9 SEM) in placebo-treated controls to 26.1 (±5.4 SEM) in guinea pigs treated with NAC/HPN-07. Similarly, the average IHC loss across the same tonotopic frequency range in placebo-treated controls (43.4±4.8) were reduced by 38% in NAC/HPN-07-treated animals (26.9±4.4). Along the basal turn of the cochlea (16-32 kHz frequency range) in placebo-treated guinea pigs, the therapeutic effects of NAC/HPN-07 treatment was even more pronounced, where the CI surgery-induced effects on average OHC and IHC loss in placebo-treated controls were reduced by 86% (97.0±1.7 versus 13.4±3.8) and 64% (50.5±6.4 versus 18.0±3.8), respectively.

What is claimed is:

1. A method of alleviating negative effects of cochlear implant surgery in a subject in need thereof comprising administering between about 50 mg/kg to about 800 mg/kg body weight of 2,4-disulfonyl α-phenyl tertiary butyl nitrone (2,4-DSPBN) or a pharmaceutically acceptable salt thereof and between about 50 mg/kg to about 800 mg/kg body weight N-acetylcysteine (NAC) or a pharmaceutically acceptable salt thereof to the subject prior to and after cochlear implant surgery, wherein the negative effects of cochlear implant surgery comprises loss of hair cells.

2. The method of claim 1 in which said administration is carried out (i) orally, (ii) locally, (iii) directly into the cochlea, (iv) systemically, or (v) intra-tympanically by instilling locally a composition, which further comprises a lubricant, prior to the subject receiving said implant.

3. The method of claim 1 in which the subject receives an implant comprising an electrode and in which said administration is carried out prior to the subject receiving said implant.

4. The method of claim 1 in which the subject receives an implant comprising an electrode, said implant having an outer coating comprising the composition.

5. The method of claim 1 in which the composition further comprises a heat sensitive gel.

6. The method of claim 1 in which said administration is carried out intravenously or topically initially, followed by oral administration.

7. The method of claim 1 in which said administration is carried out orally prior to the cochlear implant surgery, intravenously at the time or immediately prior to the cochlear implant surgery, and orally after the cochlear implant surgery.

8. The method of claim 1 in which the subject receives an implant comprising an electrode and in which said administration is carried out after the cochlear implant surgery and before turning on the electrode.

9. The method of claim 1 in which the subject belongs to an adult population, or a pediatric population.

10. The method of claim 9 in which the pediatric population is selected from neonates (birth to 1 month), infants (1 month to 2 years), developing children (2-12 years), and adolescents (12-16 years).

11. A method of treating a human subject diagnosed with sensorineural hearing loss prior to, while, and/or after undergoing cochlear implant surgery comprising administering to the subject between about 50 mg/kg to about 800 mg/kg body weight of 2,4-disulfonyl α-phenyl tertiary butyl nitrone (2,4-DSPBN) or a pharmaceutically acceptable salt thereof and between about 50 mg/kg to about 800 mg/kg body weight N-acetylcysteine (NAC) or a pharmaceutically acceptable salt thereof prior to and after undergoing cochlear implant surgery.

12. The method of claim 11 which further comprises performing auditory brainstem response (ABR) threshold recordings (measured by the sound pressure level in dB required to elicit an ABR response) at one or more test frequencies.

13. The method of claim 12 which further comprises comparing an ABR threshold recorded for the subject at the one or more test frequencies to an ABR threshold recorded for an untreated or control subject at the same one or more test frequencies.

14. The method of claim 13 in which the ABR threshold recorded for the subject at the one or more test frequencies is lower compared to that of an untreated or control subject.

15. The method of claim 12 in which ABR threshold recordings are performed at one or more test frequencies ranging from 1 to 8 kHz.

16. The method of claim 11 in which administration is carried out prior to, while, and after undergoing the cochlear implant surgery.

17. A method of reducing a loss of a plurality of hair cells in a subject prior to, while, and/or after undergoing cochlear implant surgery comprising administering to the human subject between about 50 mg/kg to about 800 mg/kg body weight of 2,4-disulfonyl α-phenyl tertiary butyl nitrone (2,4-DSPBN) or a pharmaceutically acceptable salt thereof and between about 50 mg/kg to about 800 mg/kg body weight N-acetylcysteine (NAC) or a pharmaceutically acceptable salt thereof prior to and after cochlear implant surgery that causes loss of hair cells.

18. The method of claim 17 in which said hair cells comprise inner hair cells, outer hair cells, or both.

19. The method of claim 18 in which the loss of the plurality of inner hair cells at tonotopic frequency positions ranging from 1 to 8 kHz is reduced by at least about 38% compared to that of untreated or control subjects.

20. The method of claim 18 in which the loss of the plurality of inner hair cells at tonotopic frequency positions ranging from 2 to 8 kHz is reduced by at least about 64% compared to that of untreated or control subjects.

21. The method of claim 1, further comprising administering dexamethasone to the subject.

* * * * *